US010639450B2

(12) United States Patent
McMurtry et al.

(10) Patent No.: US 10,639,450 B2
(45) Date of Patent: May 5, 2020

(54) MEDICAL DEVICE AND DELIVERY METHOD ONTO OFFSET SURFACE OF MAMMAL TISSUE

(71) Applicant: Fibralign Corporation, Union City, CA (US)

(72) Inventors: David H. McMurtry, Felton, CA (US); Michael V. Paukshto, Foster City, CA (US); Tatiana S. Zaitseva, San Jose, CA (US)

(73) Assignee: FIBRALIGN CORPORATION, Union City, CA (US)

( * ) Notice: Subject to any disclaimer, the term of this patent is extended or adjusted under 35 U.S.C. 154(b) by 902 days.

(21) Appl. No.: 14/417,089

(22) PCT Filed: Jul. 24, 2013

(86) PCT No.: PCT/US2013/051906
§ 371 (c)(1),
(2) Date: Jan. 23, 2015

(87) PCT Pub. No.: WO2014/018685
PCT Pub. Date: Jan. 30, 2014

(65) Prior Publication Data
US 2015/0202408 A1 Jul. 23, 2015

Related U.S. Application Data

(60) Provisional application No. 61/741,641, filed on Jul. 25, 2012.

(51) Int. Cl.
*A61M 25/01* (2006.01)
*A61B 5/06* (2006.01)
(Continued)

(52) U.S. Cl.
CPC ............ *A61M 25/01* (2013.01); *A61B 5/065* (2013.01); *A61B 17/0401* (2013.01);
(Continued)

(58) Field of Classification Search
CPC ................ A61B 5/065; A61B 17/3403; A61B 2017/3405; A61B 2017/3407;
(Continued)

(56) References Cited

U.S. PATENT DOCUMENTS 4,244,362 A   1/1981  Anderson
4,403,987 A * 9/1983  Gottinger ............ A61M 5/3287
                                                        604/115

(Continued)

FOREIGN PATENT DOCUMENTS

WO         00/12166 A1    3/2000

OTHER PUBLICATIONS

International Search Report and Written Opinion in International Application No. PCT/US2013/051906, dated Oct. 22, 2013.

*Primary Examiner* — Shefali D Patel
(74) *Attorney, Agent, or Firm* — DLA Piper LLP (US)

(57) ABSTRACT

A novel medical device and a method for delivery of a scaffold for treatment of secondary lymphedema and ischemia is provided. In some embodiments a catheter medical device and a magnetic guidance method are provided for delivering cell-seeded implants for guided lymphatic regeneration.

20 Claims, 9 Drawing Sheets

(51) Int. Cl.
*A61M 25/02* (2006.01)
*A61M 37/00* (2006.01)
*A61B 17/34* (2006.01)
*A61B 17/32* (2006.01)
*A61B 17/00* (2006.01)
*A61B 17/04* (2006.01)

(52) U.S. Cl.
CPC ....... *A61B 17/3403* (2013.01); *A61B 17/3468* (2013.01); *A61B 2017/00004* (2013.01); *A61B 2017/00792* (2013.01); *A61B 2017/00796* (2013.01); *A61B 2017/0403* (2013.01); *A61B 2017/0409* (2013.01); *A61B 2017/0412* (2013.01); *A61B 2017/320056* (2013.01); *A61M 25/0127* (2013.01); *A61M 25/02* (2013.01); *A61M 37/0069* (2013.01); *A61M 2025/0166* (2013.01)

(58) Field of Classification Search
CPC ... A61B 2017/3409; A61B 2017/3411; A61M 25/01; A61M 25/0113; A61M 25/0127; A61M 25/0158; A61M 2025/0166; A61M 2025/0177; A61M 2025/018; A61M 2025/09116

See application file for complete search history.

(56) References Cited

U.S. PATENT DOCUMENTS

| | | | |
|---|---|---|---|
| 4,824,435 A | | 4/1989 | Giesy et al. |
| 6,095,990 A | * | 8/2000 | Parodi ............... A61M 25/0172 600/585 |
| 2003/0154986 A1 | | 8/2003 | Fariss et al. |
| 2005/0021063 A1 | | 1/2005 | Hall et al. |
| 2008/0249395 A1 | * | 10/2008 | Shachar ................ A61B 5/06 600/409 |
| 2012/0203137 A1 | * | 8/2012 | Neuman ............ A61B 5/15003 600/576 |

* cited by examiner $s = \alpha r$
$s_1 = \alpha(r - d) = s - \alpha d$

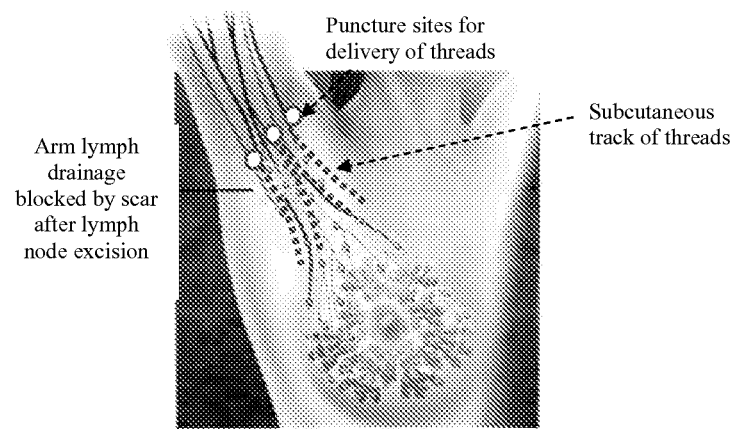
FIG. 2. The scaffold (thread or bundle of threads) connecting lymphatic systems.

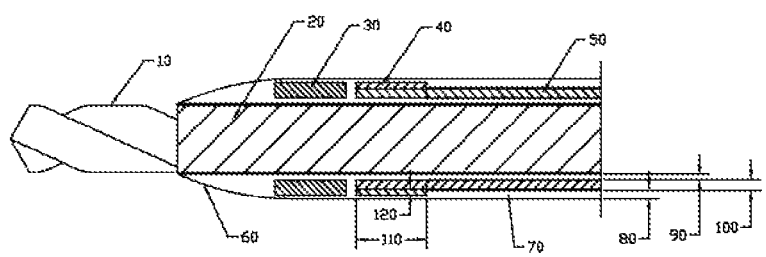
Figure 3a
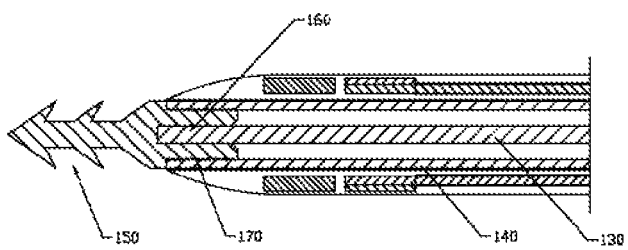 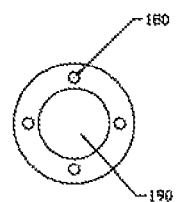
Figure 3b  Figure 3c

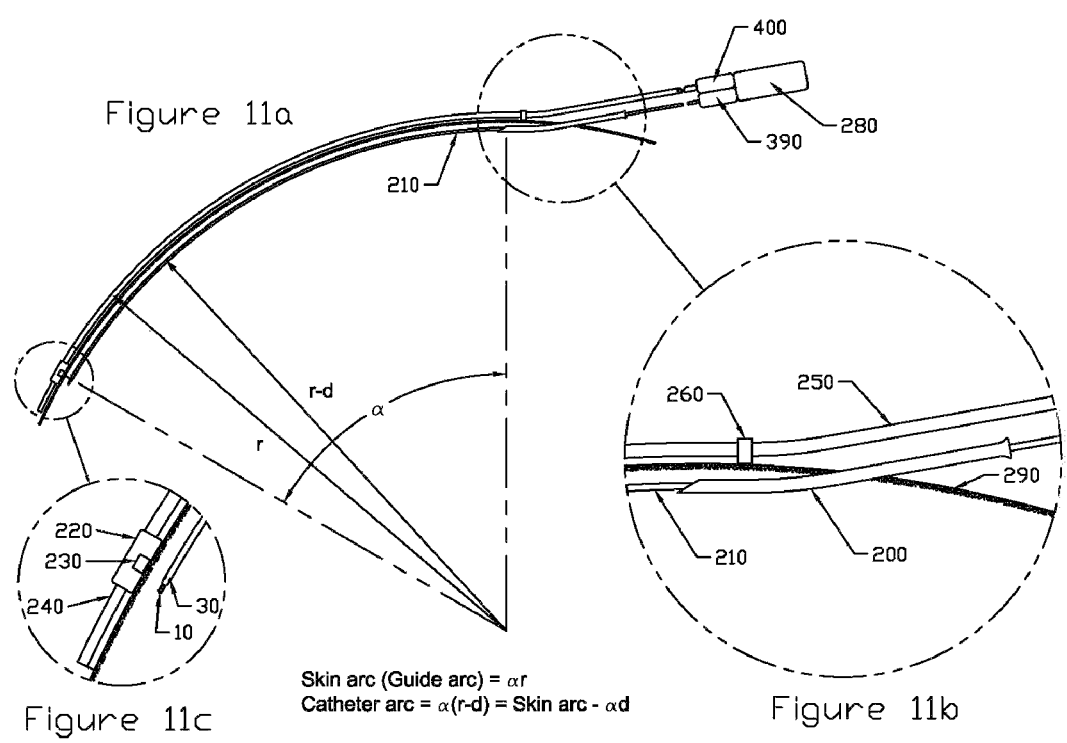

MEDICAL DEVICE AND DELIVERY METHOD ONTO OFFSET SURFACE OF MAMMAL TISSUE

CROSS REFERENCE TO RELATED APPLICATIONS

This application is a United States National Stage Application filed under 35 U.S.C. § 371 of International Application No. PCT/US2013/051906, entitled "Medical Device And Delivery Method Onto Offset Surface Of Mammal Tissue" which was filed on Jul. 24, 2013 which claims the benefit of, and priority to, U.S. Provisional Patent Application Ser. No. 61/741,641, filed Jul. 25, 2012, entitled "Catheter and Magnetic Guidance Method for Delivering Cell-Seeded Implant for Guided Lymphatic Regeneration" the entire disclosure of which is hereby incorporated by reference.

GOVERNMENT RIGHTS

This application was partially supported by the U.S. Army Medical Research and Material Command under Contract No. W81XWH-12-C-0111.

FIELD OF THE INVENTION

The present invention relates broadly to a novel medical device and method for delivery of a medical device, and more specifically to a medical device and method of deliver of a scaffold for treatment of secondary lymphedema and ischemia. In some embodiments a catheter medical device and magnetic guidance method are provided for delivering cell-seeded implants for guided lymphatic regeneration.

BACKGROUND

Lymphedema and ischemia are debilitating conditions for which limited treatment is available. Despite significant research, current treatment schemes are inadequate. In some instances, intradermal and subcutaneous delivery procedures have been tried, such as drug delivery, contrast agent delivery, gel and scaffold delivery for aesthetic and cosmetic applications, gel and scaffold delivery for repair and regeneration, cell delivery including cell plated on scaffold and gel.

Examples of common delivery methods which penetrate the skin to very small depths (0.5-1.0 mm) include a) jet injection, including needle-free injection and b) microneedles patch delivery. Standard subcutaneous methods for short distance injections would be the Mantoux technique (standard intradermal delivery method) or BD microinjection system.

However, these methods cannot be directly applied for the delivery of relatively large medical devices (millimeters and sub-millimeters size) or devices that have to be delivered into a large area in the mammalian body. For example, special methods are needed for intradermal delivery of a 100 mm long and 0.3 mm thick thread-like scaffolds. Thus, such procedures are very limited.

Another important need is the delivery of cells and growth factors into an ischemic mammal leg for treatment of critical limb ischemia. Current cell delivery systems have critical limitations, such as for example: inefficient cell retention and lack of targeted localization. Collagen, fibrin, gelatin, alginate, and matrigel have been studied as cell delivery vehicles in the form of injectable gels or three-dimensional scaffolds. While many of these materials have shown potential for success, they are not without their limitations. The issue of cell and material retention in injectable gels, as well as vascularization and nutrient diffusion in three-dimensional scaffolds, remains a challenge. The fibrin microthreads proposed recently by Cornwell and Pins have overcome these problems, but they have low mechanical strength and high degradation rate, and thus have very limited suitability. Accordingly, there is significant need for further advancement and development.

SUMMARY

In some embodiments, a novel medical device and method for delivery of a scaffold for treatment of secondary lymphedema and ischemia is provided. In some embodiments a catheter medical device and magnetic guidance method are provided for delivering cell-seeded implants for guided lymphatic regeneration.

In one aspect, embodiments of the present invention provide methods of delivery of a medical device having proximal and distal ends into a mammal tissue comprising the steps of: forming a guide line on the surface of the tissue; placing a guiding device that can move along the guide line on the surface of the tissue; deploying the medical device distal end into the mammal tissue at a desired depth d; coupling between the guiding device and the medical device distal and/or proximal end; and introducing the medical device distal end along the normal projection of the guide line to the offset surface of mammal tissue located at the distance d from the tissue surface.

In other embodiments, a method of delivery of a medical device having proximal and distal ends into a mammal tissue is provided, comprising: a guide line on the surface of the tissue and guiding device that can move along the guide line on the surface of the tissue such that the medical device distal end and the guiding device are coupled to move the medical device distal end into the mammal tissue at a constant distance d from the guiding line.

In another aspect, embodiments provide a method of delivery of a medical device having proximal and distal ends onto the offset surface of mammal tissue comprising a guide line on the surface of the tissue and a guiding device moving along the guide line on the surface of the tissue such that the medical device distal end and the guiding device are coupled to move the medical device proximal end and the guiding device to the same distance.

In some embodiments, the distal end of the medical device is introduced under control of the guiding device and/or the medical device proximal end. In some embodiments, the guiding device has a sensor and the medical device distal end generates a signal which can be sensed by the guiding device and used to control the position of the medical device distal end. In other embodiments, the guiding device has magnetic sensors and the medical device distal end generates a magnetic field which can be sensed by the guiding device and used to control the position of the medical device distal end. In some embodiment, introduction and movement of the distal end are achieved by any one or more of: drilling, slicing, shaving or abrading of the tissue using mechanical means, or evaporating of the tissue using a laser system, or by tearing the tissue under a tension applied from the proximal end.

In one example, the guiding device is comprised of a hollow, flexible track held in intimate contact with the surface of the tissue by the force of vacuum operating through holes in the bottom of the track and positioned on top of the guiding line and having a rail geometry which captures a carriage containing the sensors.

Further, in some embodiments the carriage carrying the sensors is actuated along the flexible track by a flexible C-shaped tube which has an opening along its bottom wide enough to allow clearance between the rail support and tube but narrow enough so that it is captured by the wider rail. In one example, the flexible C-shaped tube is rigidly connected to the proximal end of the catheter such that the carriage advances the same distance as the catheter. In one example, the proximal end of the flexible C-shaped tube is advanced by a servo mechanism in response to the magnetic field at the distal end of the catheter such that the normal distance between the sensors and the source of the magnetic field is maintained at the desired depth d.

In another aspect, a medical device is provided having a steerable catheter which comprises a flexible tube into which flexible devices can be inserted at the proximal end. In one example, the proximal end can carry the steering and insertion mechanism and the distal end can carry any one or more of: a sensing target, signal generator, steering ring with attached wires, drill bit, tissue shaver, slicer, rasp, laser waveguide, orifice for discharging liquid, orifice for inhaling debris, fiber optic, implant, forceps, drug delivery reservoir, probe and diagnostic device.

In some embodiment the medical device is configured to deliver a piece of tissue, scaffold, biopolymer thread or micro-thread, biopolymer filament, gel, micro-particles, decellularized tissue, fragments of lymphatic system including fragments of autologous lymph node or decellularized lymph node of animal origin, bioactive components like live cells, growth factors, peptides, drugs, drug releasing carriers.

In another aspect, a method is provided to determine the guide line on the surface of the tissue. Is some embodiments, a guide line on the surface of tissue is determined by the steps of: attaching a flexible grid over the selected area on the surface of the target tissue, that creates a grid image (positive or negative contrast) during one of diagnostic procedure like MRI, CT scan, or PET-CT; obtaining images of the target tissue and the grid by one of the diagnostic procedures indicated above; deriving a projection image of the target tissue onto the grid image; and making the guide line on the surface of the tissue using the grid attached to the surface and the images of the target tissue with the grid.

It should be understand that in some embodiments, the device provided herein may be used in other, non-medical applications. For example, in some embodiments a device system is provided comprising: a boring device having proximal and distal ends; a guiding device configured to move along a boring path defined on a surface, said guiding device comprised of a flexible guide rail and a carriage carried by the guide rail; wherein the distal end of the boring device and the guiding device are coupled to move the distal end of the boring device along the boring path at a constant distance d form the surface.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout.

FIG. 2 is a schematic diagram showing a biomimetic thread implanted under the skin in the case of lymphedema treatment;

FIGS. 3a-3b, and 3c are side views, and an end view, respectively of a medical device according to some embodiments;

FIGS. 11a-11c is a side view of the medical device deployed on a convex surface of skin tissue with enlarged side views of the proximal and distal ends.

DETAILED DESCRIPTION

The present invention relates broadly to a novel medical device and method for delivery of a medical device, and more specifically to a medical device and method of delivery of a scaffold for treatment of secondary lymphedema and ischemia. In some embodiments a catheter medical device and magnetic guidance method are provided for delivering cell-seeded implants for guided lymphatic regeneration.

Figure 1A:
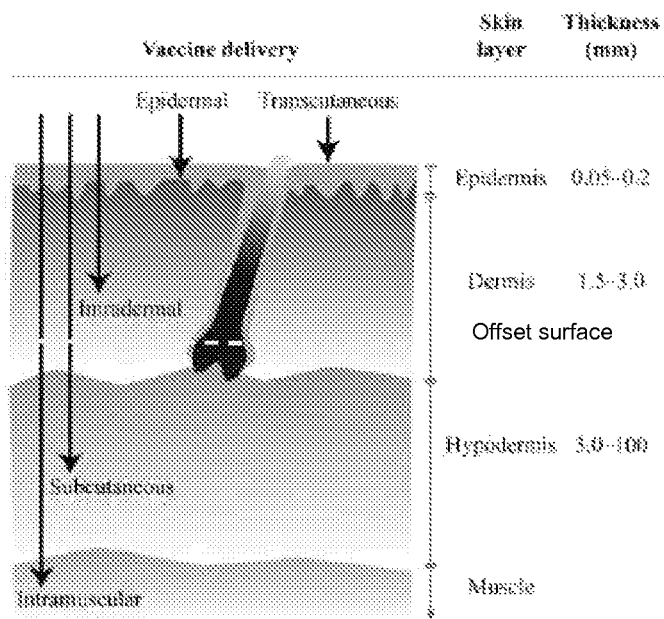
FIGS. 1a and 1b is a schematic diagram showing the "offset surface" with respect to tissue according to some embodiments.
Figure 1B:
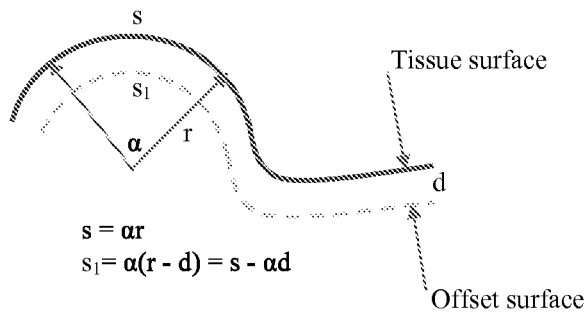
Figure 4A:
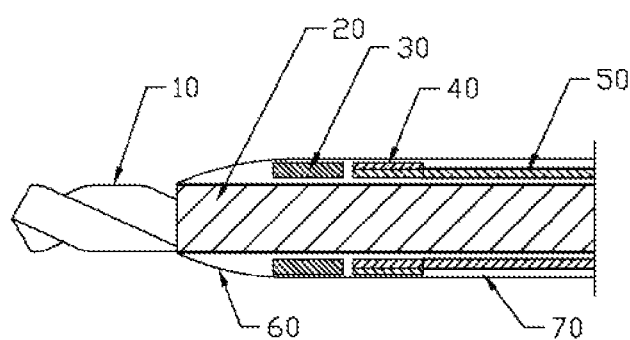
FIGS. 4a-4e are partial, side, sequential views illustrating the sequence to deploy a thread into tissue according to some embodiment.
Figure 4B:
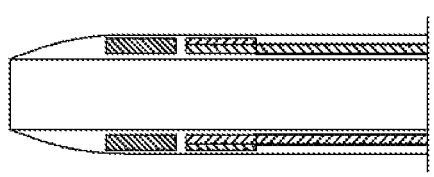
Figure 4C:
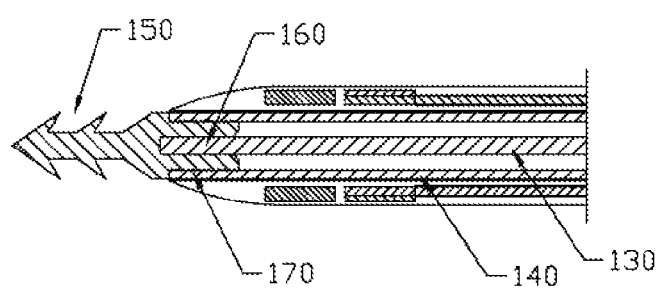
Figure 4D:
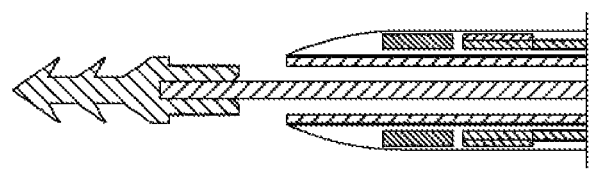
Figure 4E:
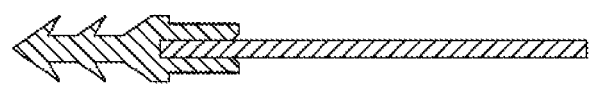

As used herein the term "offset surface" of a mammal tissue is defined as the surface of a mammal tissue located at a fixed distance from the tissue surface. Referring to FIGS. 1a and 1b, in one example, intradermal delivery is the delivery onto an offset surface located in the dermis layer of the skin.

One objective of embodiments of the present invention is to create a novel medical device for delivery of a scaffold for treatment of secondary lymphedema and ischemia, and guided lymphatic regeneration. While, embodiments are described in the context of treatment of lymphedema and ischemia, the device and method described herein are not limited to these two specific applications, and other applications for use of the delivery device and method are within the scope and spirit of the teaching and claims herein. In some embodiments, examples of the medical material that can be delivered using the method and device of the present invention are: flap of tissue, scaffold, biopolymer thread or micro-thread, biopolymer filament, gel or micro-particles, decellularized tissue, fragments of lymphatic system including fragments of autologous lymph node or decellularized lymph node of animal origin, a pack including several threads, e.g., several parallel threads encapsulated into membrane or between two membranes. The materials may also include bioactive components like live cells, growth factors, peptides, and drugs. The important requirement for the delivery procedure (with and without cells) is that it be minimally invasive. The device and method of the present invention can be used for subcutaneous or intradermal delivery.

Catheters were designed to perform a critical task inside the body while being operated from outside of the body. The distal portion of a catheter performs the task internally, while the proximal portion is controlled by the physician. Catheters are considered minimally invasive and require imaging and navigation techniques to provide feedback to the device's operator to guide the catheter properly. There are many different ways to track a catheter in the body. For example, x-ray fluoroscopy is commonly used to guide the physician to navigate the catheter to the proper position within the heart, while providing some imaging of the heart More precise and sophisticated 3D mapping techniques combining x-rays with multiple magnetic fields have been developed. For example, the Stereotaxis and Carto3 (Johnson & Johnson®) mapping systems are now finding more widespread use. These mapping systems permit the physician to more quickly and accurately guide catheters within deep body recesses. However these mapping systems are very expensive and require extensive training.

Embodiments of the present invention provide significant improvement over prior art methods and provide a much simplified mapping and guidance system which is designed for guiding a catheter along a path which lies on a plane only a few millimeters beneath the surface of mammalian tissue. As such, both the cost of the device and the training to operate it are significantly less. One example of its use would be to guide a catheter as it tunnels a few millimeters beneath the surface of the skin. Another example would be to guide a catheter as it tunnels a few millimeters beneath the surface of heart muscle tissue during heart surgery.

The preferred scaffold (matrix) that can be delivered by the invented medical device is nanoweave collagen thread or multiple threads. This scaffold is manufactured with various nanoweave properties, including aligned fibers, crimps, periodicity and angular distribution. The production process results in bioequivalent scaffolds with controlled 3D nanostructure and microstructure, controlled thickness, fibril size, and high uniformity. These scaffolds are produced from clinical grade monomeric type I collagen, engineered to a specific liquid crystal phase and manufactured under precise flow conditions to produce a thin, strong membrane which is subsequently transformed into a thread-like configuration. Their properties are a) biomimetic (i.e. approximating native tissue structure—at the nano- through macro-scales), b) high mechanical strength, c) defect-free over a large area (several $cm^2$), and e) biodegradable depending on the level of crosslinking. Various cell line testing and animal studies indicate that these tissue-mimicking devices enable rapid cell attachment, induce cell guidance and aligned cell growth, and are capable of site specific cell delivery. The scaffolds are produced as ultrathin (1-5 µm) membranes which can be further fabricated into thread-like nanopatterned scaffolds (or pseudo-fibers), using liquid-air surface tension. The individual threads can also be braided into multifiber threads. These patented novel materials present an opportunity to deliver autologous and allergenic human cells for regeneration purposes. Early work with collaborators demonstrates that the scaffolds can be used as cell carriers and when delivered to a specific site, promote regeneration.

For example, in the case of lymphedema treatment, the biomimetic thread is implanted under the skin as shown in FIG. 2. Here, the scaffold, consisting of a thread or bundle of threads has been implanted under the skin from puncture sites where a trocar has been inserted by the surgeon. The short, rigid trocar serves as the entry tunnel for the flexible catheter. The implanted thread-like scaffolds provide the guidance, migration and alignment for lymphatic endothelial and other cells and induce reconnection of the disrupted lymphatic system. Additional growth factors like VEGF-C and VEGF-D included in the threads may further speed-up the integration of the lymphatic system. The thread bridges the two functioning areas of the lymphatic system by penetrating dense scar tissue under the arm that tends to "clog up" the lymphatic channels and prevent fluid circulation.

An experiment has been conducted with nanoweave collagen thread cross-linked by 1% genipin for 24 hours (210-µm diameter in dry state). The thread hydrated for 15 minutes in PBS (400-µm diameter in wet state) was tested as a suture though the muscle of a thawed chicken thigh (previously frozen). The maximum pullout force was measured to be less than 60 g, and the stress applied to the cross-section area of the wet thread was calculated as 5 MPa.

Another important application is the delivery of cells and growth factors into the limb of mammal for treatment of critical limb ischemia. Current cell delivery systems have critical limitations such as inefficient cell retention and lack of targeted localization. Collagen, fibrin, gelatin, alginate, and matrigel have been studied as cell delivery vehicles in the form of injectable gels or three-dimensional scaffolds. While many of these materials have shown potential for success, they are not without their limitations. The issue of cell and material retention in injectable gels, as well as vascularization and nutrient diffusion in three-dimensional scaffolds, remains a challenge. The fibrin microthreads proposed recently by Cornwell and Pins have overcome these problems, but they have low mechanical strength and high degradation rate. Advantages of the thread-like scaffolds are: large surface area for cell attachment due to their open, multi-luminal structure; extended survival and maintenance of cells implanted on the threads; the aligned fibers directing cell alignment and migration; tunable mechanical properties to achieve the desired function and persistence after implantation. Purified medical grade collagen with low immunogenicity as a starting material is used. It is a substantial advantage over allografts and xenografts.

The catheter may have a mechanical positioning system and can be guided by magnetic means or ultrasound. In the case of bioactive component delivery (e.g., stem cells) the device can be further protected by removable sheath.

Embodiments of the invention provide different ways to fix or secure the device (e.g., thread) in place before removing the catheter and the sheath. The preferred method is a biodegradable barb affixed to the distal end of the thread which is thrust into the tissue by an axial force exerted by the sheath and which grips the tissue sufficiently to resist the frictional force on the thread by the sheath and catheter as they are withdrawn. An alternate method employs an external needle which punctures the skin and passes through the opening of a biodegradable ring affixed to the distal end of the thread to anchor the thread in position while the sheath and catheter are extracted. This method requires a second penetration of the skin surface at the distal end and special orientation techniques to assure the opening of the ring faces upwards towards the skin surface.

A catheter system (the medical device) is particularly suitable, albeit not limited, for delivery of a cell-seeded implant for guided lymphatic regeneration. The implant is a thread that is manufactured from a thin collagen membrane with the nanoweave structure mimicking the wall of a lymphatic vessel. The membrane is created when medical grade liquid collagen is preprocessed and coated onto a smooth plastic substrate. The membrane approximately 1 inch wide and 1-2 um thick is removed from the substrate. It is "folded" crosswise in a random fashion creating fissures and microlumens within the folds of the thread which present an attractive anchor for cell attachment. This implant technology is covered by several patents assigned to Fibralign Corporation.

The length of thread required to bridge the gap created by the destruction of lymphatic tubes is approximately 200-300 mm. The thread must be implanted in the area covering low dermis layer, hypodermis, and the interface between dermis and hypodermis. The maximum depth from the surface of the skin can be no greater than approximately 5 mm to avoid damaging major blood vessels, nerves and other critical tissues. This requires a precision drilling through soft tissue. In addition, areas of fibrotic scar tissue must be penetrated which will tend to force the drill away from its intended path.

In an exemplary embodiment, a medical device (also sometime referred to as a catheter) is shown in FIG. 3a. In some embodiments, the medical device is comprised of a rotating shaft 20 connected to a drill bit 10 (shaver, slicer or rasp) which bores a pilot hole through the soft tissue and allows the surgeon to push the body of the catheter 70 to the location where the thread 130 will be deployed. Once the final location is reached, the drill bit 10 and shaft 20 are extracted, leaving the body of the catheter 70 in place. An assembly is inserted into the lumen 190 of the catheter consisting of the thread-like scaffold 130, a tubular sleeve 140 to protect the scaffold and a biodegradable barbed anchor 150 fastened to the end of the scaffold. A schematic diagram is shown in FIGS. 3a and 3b with some exemplary and non-limiting dimensions such as 0.005 at 80, 0.003 at 90, 0.006 at 100, 0.040 at 110 and 0.004 at 120.

The steering of the catheter tip can be accomplished with a standard 4 wire steering mechanism. The wires 50 are attached at the distal end (of the medical device) to a cylindrical steering ring 40 which is bonded to the body of the catheter. The wires pass through lumens 180 in the wall of the catheter body 70. The distal end of the catheter is fabricated with a more flexible material to facilitate accurate steering of the catheter tip. The proximal end (of the medical device) is fabricated with a stiffer material to provide greater column strength. The drill creates a pilot hole for the body of the catheter. The tapered nose 60 pushes aside the tissue to permit passage of the full diameter of the catheter body.

Figure 5:
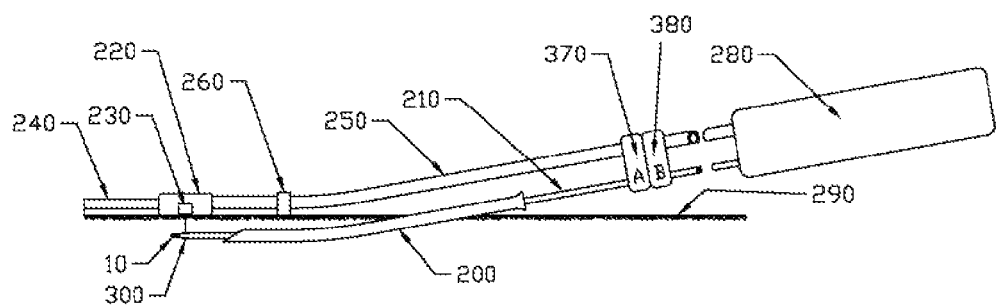
FIG. 5 is a schematic view of a carriage or guiding device and medical device distal end bounded by clamps according to some embodiments.

The sensing of the tip of the catheter is accomplished by imbedding a ring magnet 30 into the tip of the catheter (distal end of the medical device). Description of the magnetic sensor will be described later. The sequence to deploy the thread into the tissue is outlined below, and as shown in FIG. 4a-4e:

1. Advance catheter (the medical device) to deployment location (FIG. 4a)
2. Retract drill 10 and drill shaft 20 (FIG. 4b)
3. Insert assembly consisting of thread 130, thread sleeve 140 and biodegradable barbed anchor 150. Push forward into tissue to set the barbed anchor (FIG. 4c)
4. Pull back on both catheter 70 and thread sleeve 140 together to fracture the breakaway joint 170 between the barbed anchor 150 and the sleeve 140. The interface 170 between the proximal end of the barb 150 and the distal end of the sleeve 140 is designed with sufficient friction to assure that the barb will not separate from the sleeve prematurely. Breakaway design must assure that the barb retention force in the tissue is always higher than the breakaway force. (FIG. 4d)
5. Completely withdraw catheter 70 and thread sleeve 140 together. This assures that the thread 130 can only contact the inner wall of the sleeve 140, but not the inner wall of the catheter. (FIG. 4e)
6. Withdraw the trocar 200 (shown in FIG. 5) and seal the wound in an appropriate manner The major components for the catheter system are shown in FIG. 5. A flexible guide rail 240 (coincident with the guide line) is held tight to the patient's skin 290 with vacuum. The base of the rail has an internal vacuum plenum 340 with holes 330 on the bottom. Good contact with the skin can be improved by coating the skin with a thin layer of a suitable material which is troweled smooth. The coating could also have a tacky surface to increase friction with the bottom of the guide rail. A layer of tape with a smooth surface fastened to the skin could also be used. Care would have to be taken to avoid wrinkles when it follows a curved path.

Running along the rail is a carriage 220 (the guiding device) which houses two magnetic sensors 310 and 320. They detect the magnet 30 imbedded in the tip of the catheter (distal end) which lies directly beneath at a normal distance d. The carriage's linear motion is controlled by a flexible C-shaped carriage actuator tube 250 which straddles the rail 240. The actuator tube 250 is connected crossways to the proximal end of the catheter with a pair of clamps 370 and 380. When the surgeon advances the catheter, the carriage actuator tube 250 advances by the same amount. The carriage actuator tube 250 passes through a strain relief 260 which absorbs sideways forces and assures that the C-shaped tube meshes smoothly with the rail 240.

The drive motor mechanism 280 which powers the drill shaft 20 is located in a housing along with the mechanism to operate the steering wires 50.

Figure 6:
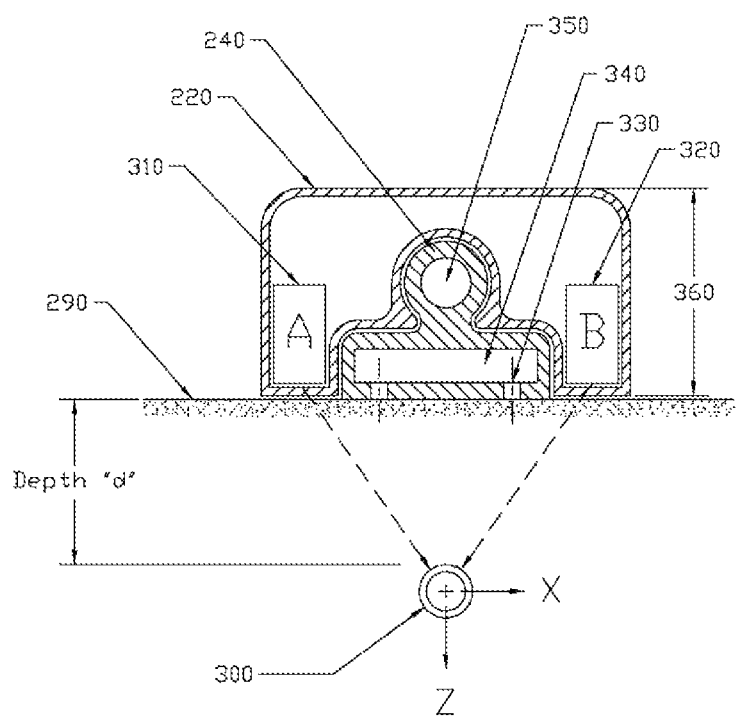
FIG. 6 is a side view of the carriage or guiding device and medical device distal end according to some embodiments.

The end view of the magnetic sensor operation is shown in FIG. 6. The magnetic sensors A 310 and B 320 typically will use Hall effect technology to achieve high accuracy. The two sensors mounted in the carriage 220, straddling the central guide rail 240 and separated by a known distance. They are mounted as close to the bottom of the carriage as possible to minimize the distance to the magnet. The dimensions shown are typical of those required. The basic method of determining the location of the magnet is as follows:

X Sensing
  A=B magnet on center
  A>B magnet to left of center
  A<B magnet to right of center
Z Sensing
  (A+B)/2=high Z is small (shallow)
  (A+B)/2=low Z is large (deep)

These signals would be processed and the results displayed on a target screen which would give the surgeon feedback to operate the steering mechanism.

FIG. 6 also shows the location of the vacuum plenum 340 and vacuum holes 330 which allow the rail 240 to grip the surface of the skin 290. Note that the material in the center portion 350 of the rail 240 has been removed. This permits the rail 240 to have improved sideways flex. It also assures better manufacturability since the thickness of all the wall sections in the guide rail are approximately equal.

Figure 7:
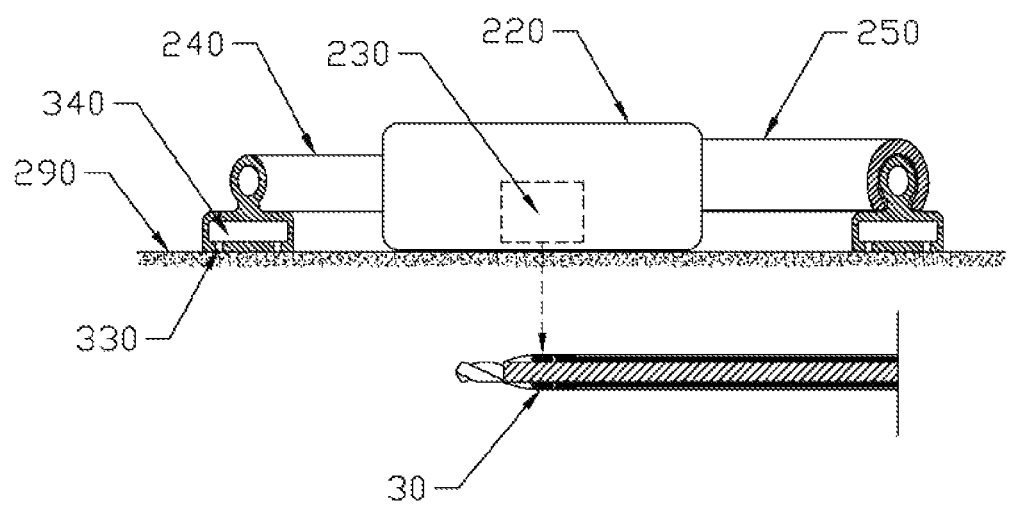
FIG. 7 is a side view of a sensing system according to some embodiments.
Figure 8:
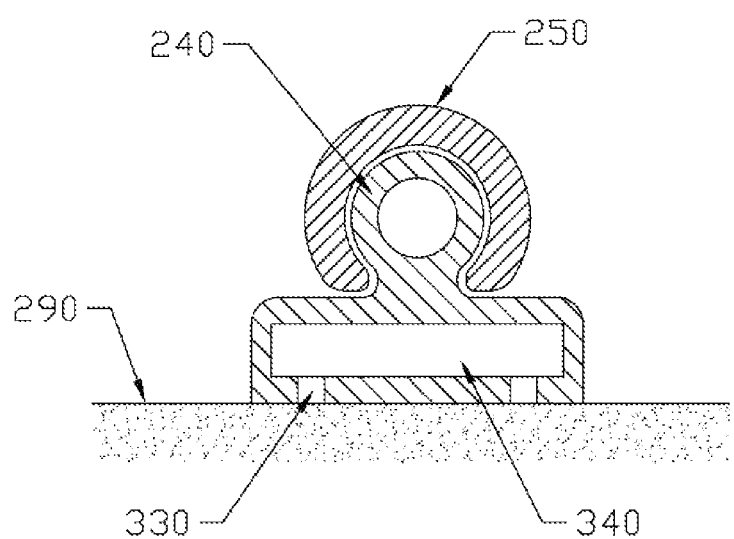
FIG. 8 is a side view of a guiding rail or guiding line with the guiding device actuator according to some embodiments.

A side view of the sensing system is shown in FIG. 7. The carriage 220 with its magnetic sensors 230 is positioned directly above the tip of the catheter. A sectional view of the guide rail 240 and flexible carriage actuator tube 250 shows how the actuator tube 250 straddles and is held in place by the guide rail 240. The actuator tube 250 is firmly affixed at its distal end to the carriage 220. FIG. 8 shows an end view of the actuator tube 250 and guide rail 240.

A guide line is marked on the surface of the skin by the surgeon indicating the path required for the thread to follow beneath the surface of the skin. This guide line can be determined by a unique mapping technique. A flexible grid, which is attached to the surface of the skin 290 with a suitable adhesive, is visible to diagnostic procedures such as MRI, CT scan or PET-CT. The grid is composed of an array of wires fabricated from a material, such as gadolinium, iron or iron oxide, selected to produce a high contrast image for the particular diagnostic procedure. The grid pattern is superimposed over the image of the tissue obtained by one of these procedures. While the grid still remains affixed to the surface of the skin, the surgeon is then able to plot the best route for marking the guide line onto the surface of the skin 290.

He then aligns the flexible carriage guide rail 240 on top of the guide line and affixes it to the skin surface 290 by activating the vacuum source which sucks the guide rail into intimate skin contact.

The surgeon inserts the distal end of the flexible carriage actuator tube into the strain relief 260 which is an integral part of the proximal end of the guide rail 240.

He then inserts the trocar 200 subcutaneously at the beginning point of the guide line, parallel to the guide line and at the desired depth d. He then inserts the distal end of the catheter into the trocar. He pushes the catheter into the trocar until the tip emerges. Since the trocar is typically a metallic device of uncertain magnetic permeability, the signal from the magnetic sensors cannot be relied upon until the magnet emerges from the trocar. The point of emergence can be detected by a sudden increase in the magnetic sensor outputs.

Figure 9:
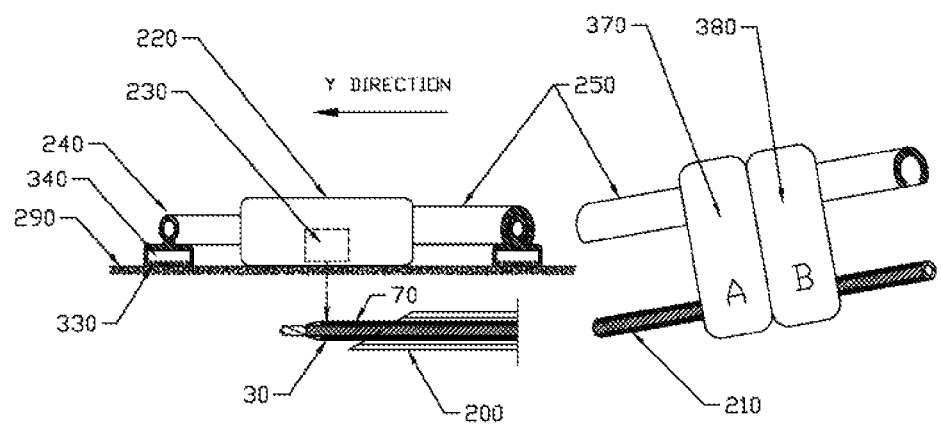
FIG. 9 is a schematic, assembly view showing the alignment of the medical device proximal end and the guiding device.

As soon as the catheter emerges from the tip of the trocar, the drill is turned off and the catheter position is carefully maintained. At this point the catheter and magnetic sensors must be synchronized. The alignment procedure is shown in FIG. 9 and described below:

Align the carriage 220 to maximize the sensor signals.

If required, release the vacuum and reposition the proximal end of the guide rail 240. However turning off the vacuum would cause the entire rail to disengage from the guide line and would require repositioning along its entire length. Since only a short length of the proximal end of the guide rail need be repositioned, the vacuum system would be preferably designed with two separate chambers: proximal and distal. Vacuum in both chambers would be normally engaged. However if a short length of the proximal end needed repositioning, only the proximal chamber would be deactivated and reactivated after repositioning without disturbing the much longer distal chamber.

The absolute Z depth d of the catheter tip can be determined from calibration tables that have been previously developed by laboratory testing of representative tissue samples. Magnetic permeability of tissue is similar to that found in a vacuum.

Lock both connector clamps A 370 and B 380 between the catheter 210 proximal end and carriage actuator tube 250 proximal end The zero point for the Y direction of the carriage 220 has now been established The catheter 210 can only be advanced until the first clamp A 370 contacts the proximal end of the trocar 200. The drilling and advancement operation must stop until the clamps are shifted upstream. The procedure for doing this is described below and is shown is FIG. 10.

Figure 10A:
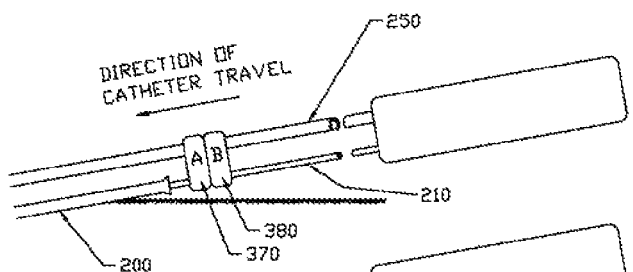
FIGS. 10a-10c are schematic diagrams illustrating a realignment procedure of the medical device according to some embodiments.

Clamp pair A 370 and B 380 has reached limit of travel (FIG. 10a)

Figure 10B:
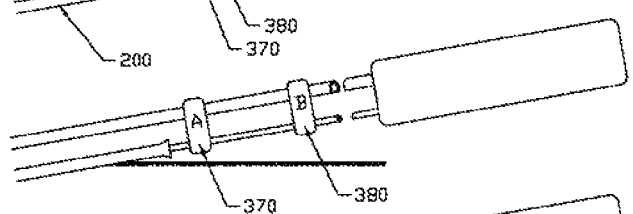

Unclamp B 380, slide to right and re-clamp (FIG. 10b)

Figure 10C:
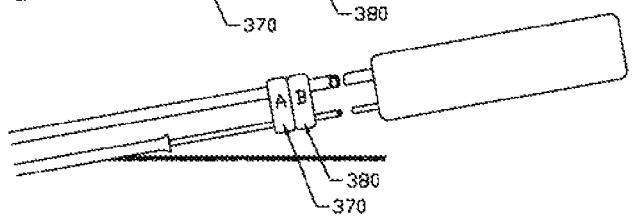

Unclamp A 370, slide to right to touch B 380 and re-clamp (FIG. 10c)

The maximum practical distance between the clamp pair 370, 380 and the trocar 200 is governed by the buckling strength of the catheter 210 and actuator tube 250. Since the insertion operation requires pushing on long slender columns, Euler buckling limits apply. The clamp-to-trocar distance will always be less than the clamp-to-strain relief distance (refer back to FIG. 5). The frictional resistance of the actuator tube 250 as it slides through the strain relief 260 and along the rail 240 will be predictable since there will be few contaminants to impede its motion. Hence the buckling limits will also be predictable.

However the drilling and frictional forces exerted on the catheter present a different problem. The drill tip will encounter fibrotic tissue of varying resistance so the buckling limit will be difficult to predict. The surgeon must determine from practical experience the maximum clamp-to-trocar distance.

The above solution describes a mechanical double clamp method to link and synchronize the two linear motions: that of the catheter and that of the sensor carriage. However it would be possible to have a linear encoder along the length of the catheter that would create a position signal with respect to a stationary reference point (e. g. a point on the trocar). This in turn could control an electro-mechanical linear actuator translating the sensor carriage 220 in the Y-direction that would remain in synchronism with the catheter tip. The Z distance for each X-Y incremental point could be pre-determined and stored in control memory. In this manner the surgeon would only have to concentrate on advancing the catheter. The 4 wire steering system would automatically guide the tip depth d (Z) and the sideways motion (X) while the surgeon would provide the Y-motion. There would be no need for clamp manipulation. While this is a more complex and expensive system, it could potentially provide greater accuracy and reduced procedure time.

In the case of the curved body surface (e.g. beating heart) the distal end of the catheter travels a different distance than the carriage. For convex surfaces as shown in FIG. 11, the catheter travels less distance than the carriage; for concave surfaces, it travels more. In these cases, the actuator tube 250 and catheter 210 are not rigidly connected by clamps. They would be replaced with system whereby the surgeon provides the forward motion of the catheter 210 using mechanism 390. But the forward motion of the carriage 220 would be operated by a computer controlled servo system 400 which would continuously calculate the position of the catheter tip and control the carriage motion to position the sensor 230 directly above the magnet 30 to enable the steering mechanism to maintain the required depth of penetration d.

In FIG. 11, r is the radius of curvature of the surface of the skin which can also be considered to be the radius of curvature of the sensors riding in the carriage. The arc length of the carriage travel is $\alpha r$. The radius of curvature of the catheter is $r-d$. The arc length of the catheter travel is $\alpha(r-d)$.

It could also be envisaged that the Y-motion of the catheter could be provided by a linear actuator. This next step of automation would eliminate the requirement for surgeon to directly control the drilling portion of the operation.

It could also be envisaged that the mechanical drilling mechanism can be replaced by a Nd-YAG or $CO_2$-laser system. The guiding efficiency can be improved by the use of array of magnetic sensors. Other types of sensing can be used as well.

Examples

The following examples are provided for illustration purposes only, and are not intended to limit the scope of the present invention in any way.

Percutaneous transmyocardial revascularization (PTMR) is performed by a cardiologist in the cardiac catheterization laboratory. After the induction of local anesthesia, the cardiologist inserts a catheter into an artery in the leg to access the heart. A laser is then fed through the catheter and used to create tiny holes in the heart muscle. These holes become channels for blood to flow to oxygen-starved areas of the heart. PTMR is currently being used on patients who have not responded to other treatments such as medicines, angioplasty, or coronary artery bypass surgery.

Transmyocardial laser revascularization (TMLR) involves the use of a laser to create tiny channels in the lower left chamber of the heart (the left ventricle), which may increase blood flow within the heart. Surgeons make an incision in the left side of the chest. While the heart is still beating, the surgeons use the laser to make between 20 and 40 tiny (one-millimeter-wide) channels through the oxygen-deprived heart muscle and into the left ventricle. These channels give a new route for blood to flow into the heart muscle, which may reduce the pain of angina. TMLR is generally considered less invasive than open heart procedures. It involves only a small incision, and patients usually do not need a blood transfusion. And because the procedure is done on a beating heart, surgeons do not need to use a heart-lung machine.

Figures 12A, 12B:
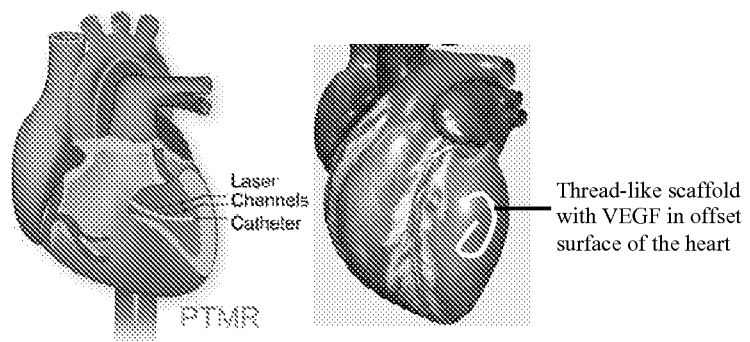
FIGS. 12a-12b are schematic representations of a mammalian heart having a thread-like scaffold in the offset surface of the heart according to some embodiments.

These two procedures unfortunately do not provide a long term improvements for patients and have now very limited use. The invented delivery device can be combined with the laser drilling method and deliver thread-like scaffolds filled with VEGF-A. Moreover, the scaffold can be delivered into an offset surface of the beating heart with only one incision, as shown in FIGS. 12a and 12b.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

We claim:

1. A method of delivery of a medical device having a proximal end and a distal end into a mammal tissue, comprising the steps of:
   forming a guide line on a surface of the mammal tissue;
   placing a guiding device, comprised of a flexible guide rail and a carriage carried by the flexible guide rail that can move along the flexible guide rail, on the surface of the mammal tissue;
   fixing the flexible guide rail on the surface of the mammal tissue along the guide line;
   deploying the distal end of the medical device, into the mammal tissue at a desired depth d;
   coupling the guiding device and the distal end and/or the proximal end of the medical device; and
   introducing the distal end of the medical device into the mammal tissue and moving the distal end of the medical device substantially along a line formed by a normal projection of the guide line to an offset surface of the mammal tissue located at the desired depth d from the surface of the mammal tissue.

2. The method according to claim 1, wherein the distal end of the medical device is introduced under control of the guiding device and/or the proximal end of the medical device.

3. The method according to claim 1, wherein the guiding device has a sensor and the distal end of the medical device generates a signal which can be sensed by the guiding device and used to control a position of the distal end of the medical device.

4. The method according to claim 1, wherein the guiding device has magnetic sensors and the distal end of the medical device generates a magnetic field which can be sensed by the guiding device and used to control a position of the distal end of the medical device.

5. The method according to claim 1, wherein the medical device is a steerable catheter comprised of a flexible tube into which flexible devices can be inserted at a proximal end of the steerable catheter.

6. The method according to claim 1, wherein the proximal end can carry a steering and insertion mechanism and the distal end can carry a sensing target, a signal generator, a steering ring with attached wires, a drill bit, a tissue shaver, a slicer, a rasp, a laser waveguide, one or more orifices for discharging a liquid, one or more orifices for inhaling debris, a fiber optic, an implant, forceps, a drug delivery reservoir, a probe or a diagnostic device.

7. The method according to claim 1, wherein the introduction and the movement of the distal end are achieved by any one or more of: drilling, slicing, shaving or abrading of the tissue using mechanical means, evaporating of the tissue using a laser system, and by tearing the tissue under a tension applied from the proximal end.

8. The method according to claim 1, wherein the medical device can deliver a piece of tissue, a scaffold, a biopolymer thread or micro-thread, a biopolymer filament, a gel, microparticles, a decellularized tissue, fragments of a lymphatic system including fragments of an autologous lymph node or a decellularized lymph node of animal origin, or bioactive components like live cells, growth factors, peptides, drugs or drug releasing carriers.

9. The method according to claim 1, wherein the guide line on the surface of the tissue is determined by the following method:
   attaching a flexible grid over a selected area on the surface of the tissue, that creates a grid image having positive or negative contrast during one of diagnostic procedures MRI, CT scan, or PET-CT;

obtaining images of the tissue and the grid by one of the diagnostic procedures indicated above;

deriving a projection image of the tissue onto the grid image; and making the guide line on the surface of the tissue using the grid attached to the surface and the images of the tissue with the grid.

10. The method according to claim 1, wherein the mammal tissue is a mammal organ or skin.

11. The method according to claim 1, wherein the guiding device is comprised of a hollow, flexible track held in intimate contact with the surface of the tissue by a force of vacuum operating through holes in a bottom of the track and positioned on top of the guide line and having a rail geometry which captures the carriage containing one or more sensors.

12. The method according to claim 11, wherein the carriage carrying the one or more sensors is actuated along the flexible track by a flexible actuator rod with a cross-sectional geometry which is constrained by a track geometry so that the actuator rod follows a path governed by the track.

13. The method according to claim 12, wherein the flexible actuator rod is rigidly connected to a proximal end of a catheter such that the carriage advances a same distance as the catheter.

14. The method according to claim 13, wherein a proximal end of the flexible actuator rod is advanced by a servo mechanism in response to a magnetic field at a distal end of the catheter such that a normal distance between the one or more sensors and a source of the magnetic field is maintained at the desired depth d.

15. A medical device system for delivery of a medical device into a mammal tissue, the medical device system comprising:

the medical device having a proximal end and a distal end; and a guiding device comprised of a flexible guide rail and a carriage carried by the flexible guide rail that can move along the flexible guide rail;

wherein the flexible guide rail can be fixed on a surface of the mammal tissue along a guide line defined on the surface of the mammal tissue, and wherein the proximal end and/or the distal end of the medical device and the guiding device are coupled to introduce the distal end of the medical device into the mammal tissue and to move the distal end of the medical device substantially along a line formed by a normal projection of the guide line to an offset surface of the mammal tissue located at a distance d from the surface of the mammal tissue.

16. The medical device system according to claim 15 wherein:

the flexible guide rail is comprised of: a base having an internal vacuum plenum formed therein, said base having a plurality of holes formed in a bottom surface of the base and configured to provide contact with the surface of the tissue by a force of vacuum operating through the holes in the bottom surface of the base; and the carriage houses one or more magnetic sensors.

17. The medical device system according to claim 16 further comprising: a flexible actuator rod having a cross-sectional geometry configured to be constrained by the flexible guide rail so that the flexible actuator rod follows a path governed by the guide rail.

18. The medical device system according to claim 17 wherein a proximal end of the flexible actuator rod is advanced by a servo mechanism in response to a magnetic field at the distal end of the medical device such that a distance between the one or more magnetic sensors and a source of the magnetic field is maintained at the distance d.

19. The medical device system according to claim 17 wherein the flexible actuator rod is rigidly connected to the proximal end of the medical device such that the carriage advances a same distance as the medical device.

20. The medical device system according to claim 15 wherein the medical device is configured to generate a magnetic field at the distal end of the medical device which is sensed by the guiding device and used to control a position of the distal end of the medical device.

* * * * *